United States Patent [19]

Komiya

[11] 4,018,229

[45] Apr. 19, 1977

[54] APPARATUS FOR LIGATION OF AFFECTED PART IN COELOMA

[75] Inventor: Osamu Komiya, Hachioji, Japan

[73] Assignee: Olympus Optical Co., Ltd., Tokyo, Japan

[22] Filed: Sept. 10, 1975

[21] Appl. No.: 612,253

[30] Foreign Application Priority Data

Sept. 13, 1974  Japan .......................... 49-110382
Sept. 13, 1974  Japan .......................... 49-110383

[52] U.S. Cl. ............................................. 128/326
[51] Int. Cl.² ........................................ A61B 17/12
[58] Field of Search ................................... 128/326

[56] References Cited

UNITED STATES PATENTS

| 1,855,546 | 4/1932 | File | 128/326 |
| 2,012,776 | 8/1935 | Roeder | 128/326 |
| 2,610,631 | 9/1952 | Calicchio | 128/326 |
| 3,476,114 | 11/1969 | Shannon et al. | 128/326 |
| 3,665,926 | 5/1972 | Flores | 128/326 |

Primary Examiner—Channing L. Pace
Attorney, Agent, or Firm—Ostrolenk, Faber, Gerb & Soffen

[57] ABSTRACT

An apparatus for ligation of affected part in coeloma comprises an inner and an outer flexible tube. A ligature or tie-up thread is provided with a loop formation, one end of which is disposed within the inner tube. The outer tube houses the loop formation, the inner tube and a pair of holding wires which are associated with the loop formation. In use, the outer tube is inserted into a coeloma and then retracted relative to the inner tube to move the loop formation out of the outer tube, whereupon the holding wires cooperate with the loop formation to extend it into an enlarged loop, which is then engaged with an affected part in the coeloma. Subsequently, one end of the loop formation is externally pulled through the inner tube, reducing the area of the loop for the purpose of ligation of the affected part.

9 Claims, 15 Drawing Figures

FIG. 1 PRIOR ART
FIG. 2 PRIOR ART
FIG. 3
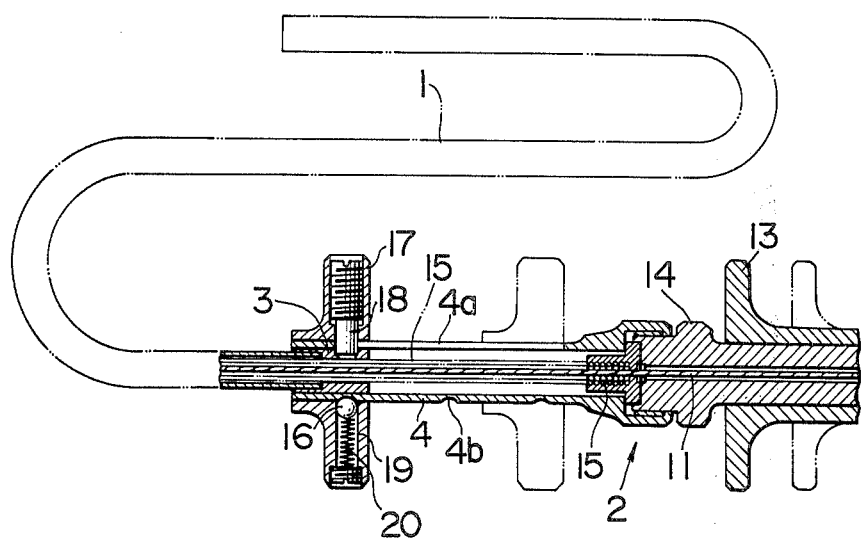

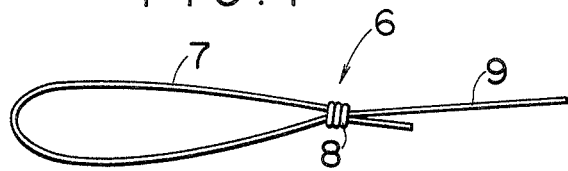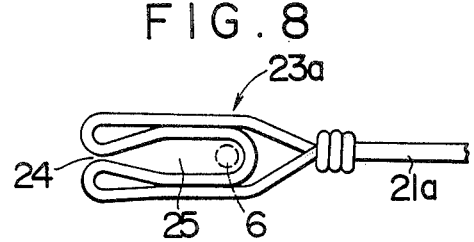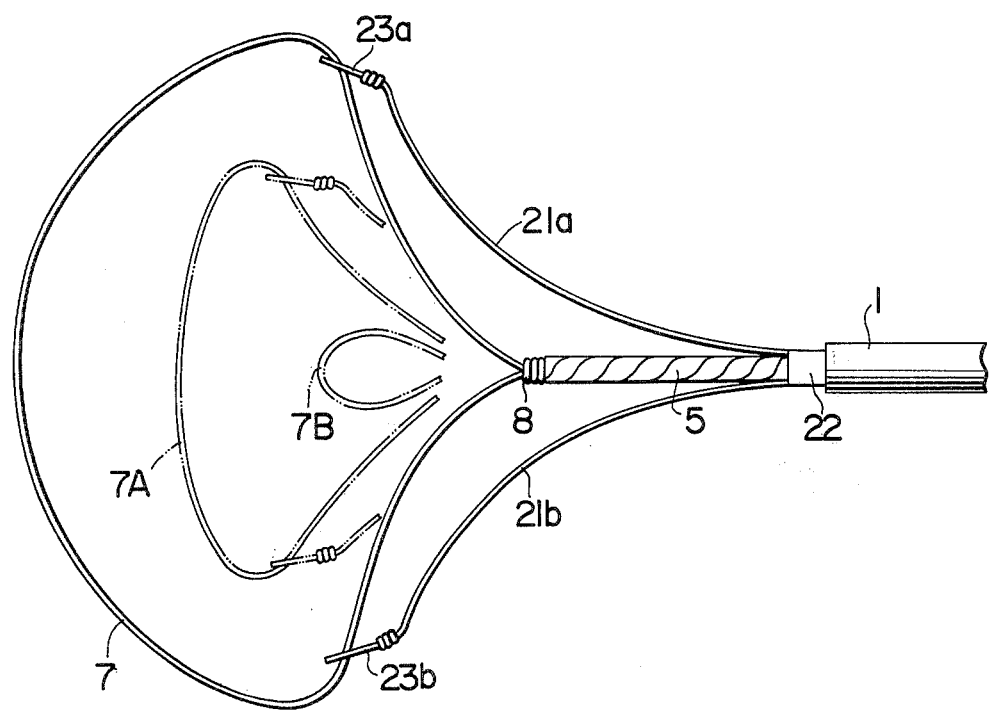

APPARATUS FOR LIGATION OF AFFECTED PART IN COELOMA

BACKGROUND OF THE INVENTION

The invention relates to an apparatus for ligation of affected part in coeloma, and more particularly to such apparatus which employes holding wires to facilitate and assure the formation of a loop.

An electric searing iron or electric coagulation member is used in a medical operation in order to remove a projecting affected part such as polyp formed in a coeloma, with the visual aid of an endoscope. However, the complexity and the safety of the instruments used present a problem in performing an operation with such instruments, and there is a risk that the removal of the affected part may result in a failure to stop bleeding. To overcome such difficulties, there has been proposed in Japanese Laid-Open Patent Publication No. 71,090/1973 the concept for a ligation of the root of the projecting affected part with a length of thread while controlling the operation by observing with an endoscope. The ligated tissue of the affected part is thus laid out of circulation of the blood to cause a necrosis for natural removal. This involves no risk of bleeding to thereby assure a safe operation, and also permits a specimen of the tissue to be picked as by forceps without involving danger. In this manner, the affected part can be safely treated.

A conventional ligature used in the prior art apparatus comprises a plurality of thin filaments twisted together, as shown in FIG. 1, so that when it is inserted into a forceps conduit of the endoscope or introduced into a coeloma, it becomes wetted by moisture or blood fluid present therein to be untwisted or disengaged as illustrated in FIG. 2. As a result, it is sometimes impossilbe to form a loop of the ligature which must be provided for engagement with and ligation of the affected part.

Additionally, a conventional ligation apparatus comprises a flexible tube having a loop formation merely exposed through the distal end thereof, which formation cannot be extended to a larger size. In addition, the loop configuration is not assured. As a consequence, it is extremely difficult, if not impossible, to engage the loop with the projecting affected part in the coeloma. Such a conventional ligation apparatus is illustrated in FIG. 15 and will be further described later.

SUMMARY OF THE INVENTION

Therefore, objects of the invention are the provision of an apparatus for ligation of an affected part in coeloma including a ligature having a loop formation which can be forcibly opened by holding wires into a loop of an increased size and a stable and desired configuration, and also the provision of an apparatus for ligation of an affected part in coeloma of the kind described which uses a ligature comprising a single or a plurality of filaments which are knitted in a manner such that it cannot be twisted or untwisted when wetted by moisture or body fluid.

In the apparatus of the invention, a pair of holding wires, which are normally urged to be separated from each other, support a loop formation in the ligature, and helps extending the loop formation into a loop of a desired size and configuration, even when the ligature is twisted. In this manner, ligation of a large sized projecton is enabled, and the ligation operation facilitated with the aid of an endoscope. The use of the ligature which comprises a single or a plurality of filaments knitted together prevents a twisting thereof, so that the achievement of a loop of a required size is always assured by preventing an untwisting or twisting of the ligature when it is wetted by moisture or body fluid when it is inserted into a forceps conduit of the endoscope or into the coeloma, thus resulting in a more simplified and positive ligation operation.

BRIEF DESCRIPTION OF THE DRAWINGS

FIG. 1 is a fragmentary enlarged plan view of a conventional ligature;

FIG. 2 is a plan view showing a twisted conventional ligature;

FIGS. 3 and 4 are fragmentary longitudinal sections of the apparatus according to one embodiment of the invention;

FIGS. 6 and 7 are plan views illustrating exemplary manners of tying a ligature;

FIG. 8 is a plan view showing one exemplary arrangement of the holding wires which hold the ligature;

FIG. 9 is a plan view showing a manner of forming the ligature into a loop;

DETAILED DESCRIPTION OF THE PREFERRED EMBODIMENT

Figure 4:
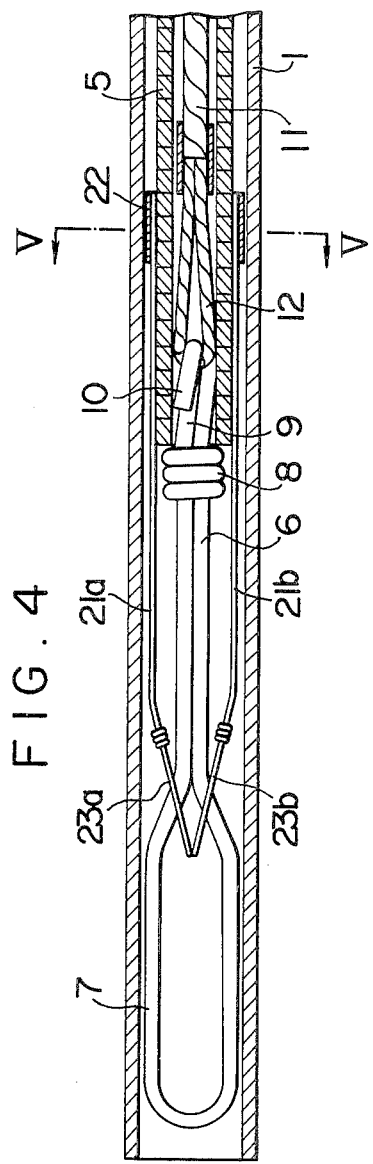
Figure 5:
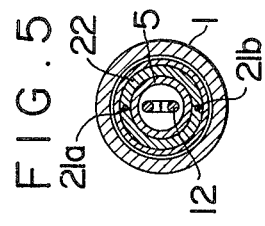
FIG. 5 is a cross section taken along the line V—V shown in FIG. 4, showing the internal construction of the apparatus.

Referring first to FIGS. 3 to 5, there is shown an apparatus for ligation of affected part in coeloma which is constructed in accordance with the invention. In FIG. 3, the apparatus includes an outer flexible tube 1, the proximate end of which is connected with a manual operation section 2. Specifically, the outer tube 1 is secured to a short sleeve of the section 2 which is in turn slidably disposed within a tubular housing 4 of the section 2. As illustrated in FIG. 4, the outer tube internally houses an inner flexible tube 5 which is formed as a close pitched coil, and a ligature 6 having a loop formation 7 which is located adjacent to the inner end of the inner tube 5. A knot 8 is formed in the ligature and has a size such that it cannot be pulled into the opening of the inner tube 5. The free end 9 of the ligature 6 extends into the inner tube 5 and is folded therein for engagement with a hook 12 formed at the inner end of an operating wire 11 which extends through the inner tube 5. The proximate end of the operating wire 11 is fixedly attached to a tying operator 13 (see FIG. 3) of the manual operation section 2. The tying operator 13 slidably fits on a support member 14 of the tubular housing 4, and operates to reduce the size of a loop formed by the loop formation 7 by pulling the end 9 of the ligature into the inner tube 5 through the operating wire 11 and the hook 12, when the tying operator 13 is moved in a direction away from the coeloma.

At its inner end, the support member 14 is provided with a fixed sleeve 15 which supports the proximate end of the inner tube 5 and prevents its axial movement. The tubular housing 4 surrounds the fixed sleeve 15 and threadably engages with the support member 14. The tubular housing 4 has an axially extending guide slot 4a, and in its outer periphery is formed a plurality of circumferentially extending grooves 4b, which are three in number in the example shown. The grooves 4b are located at equi-spaced intervals. The grooves 4b cooperate with a ball 16 to be described later to form a click stop mechanism. A knob 17 loosely fits the outer periphery of the tubular housing 4 and is secured to the sleeve 3 by a set screw 18 which extends into the slot 4a. By moving the knob 17 to the right, as viewed in FIG. 3, together with the sleeve 3, the outer tube 1 can be moved to the right or toward the manual operation section 2. A bore 19 extends radially through the knob 17, and receives the ball 16, which is resiliently urged by a spring 20. Thus, when the knob 17 is moved along the length of the tubular housing, the ball 16 engages either one of the grooves 4b for momentarily interrupting the movement of the knob 17.

Figure 6:
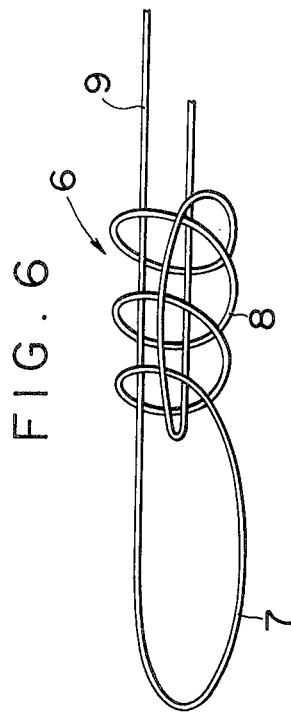

Referring to FIG. 6, the ligature 6 comprises a single suture thread, a metal wire or a knitted thread as will be described later, having a degree of resiliency, and which is tied as indicated. Specifically, three loops are formed in the ligature in order to form a knot 8, one end of the thread being extended through the knot 8 to provide a pulling end 9. The other end is turned back outside the knot 8 and then extended through a loop formation 7 and the knot 8 and is strongly pulled, whereupon the knot 8 is ultimately formed as shown in FIG. 7. The friction of the thread material itself prevents a loosening of the knot 8, and the loop formed by the loop formation 7 can be reduced in size by pulling the end 9. It should be understood that the number of loops used in forming the knot 8 is not limited to the example shown.

In accordance with the invention, there is provided a pair of holding wires 21a, 21b for extending the loop formation 7 of the ligature, as illustrated in FIG. 4. The holding wires 21a, 21b are disposed on the opposite sides of the loop formation 7 in the same general plane as the latter, and have their one end secured by a fitting ring 22 positioned against the inner periphery of the inner tube 5, as shown in FIG. 5. The holding wires are formed of a resilient material such as metal wires so that their distal ends are normally urged to be separated from each other, as illustrated in FIG. 9. The distal end of the holding wires 21a, 21b is formed with a capture 23a, 23b by bending the wire material itself. FIG. 8 shows the capture 23a formed in the holding wire 21a which comprises an outer loop and an inner, reentrant loop, defining an opening of a size which is less than the thickness of the ligature 6 and also defining a ligature receiving space 25. Normally, the oppositely located lengths of the loop formation 7 in the ligature 6 are received in the spaces 25 of the captures 23a, 23b, as shown in FIG. 4. However, the ligature 6 can be disengaged from the captures through the openings 24, by applying a force in excess of given value to the holding wires. When the holding wires 21a, 21b are moved out of the outer tube 1 together with the loop formation 7, the latter can be extended into a loop of an increased size by the resilience of the holding wires 21a, 21b.

Figure 10:
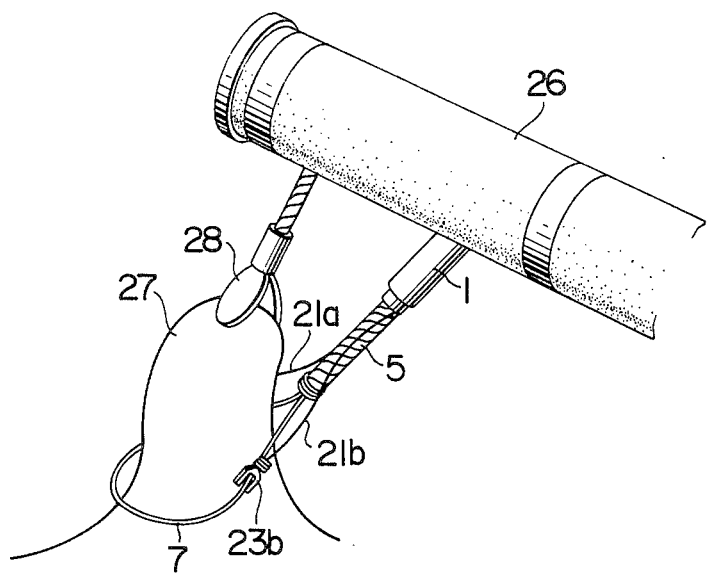
FIGS. 10 to 12 are perspective views illustrating one manner of ligation.

In use, the ligature 6 is tied in the manner mentioned previously, and its one end is engaged with the hook 12 of the operating wire 11. The knob 17 may be used to move the outer tube 1 forwardly so that the loop formation 7 of the ligature 6 can be received within the outer tube 1. This condition is illustrated in FIG. 4. Under this condition, the outer tube is inserted into a coeloma which is being observed by an endoscope 26, as shown in FIG. 10. The distal end of the outer tube 1 is moved to the proximity of an affected part 27 which is in the form of a projection, and the knob 17 is retracted in the manual operation section 2 while holding the affected part 27 against movement by means of forceps 28. When the knob 17 is retracted to a position shown in phantom lines in FIG. 3, for example, the rearward movement of the outer tube 1 exposes the loop formation 7 into the coeloma. As a consequence, the loop formation 7 is allowed to extend due to its own resiliency as well as by the bias applied by the holding wires 21a, 21b, thus forming a loop. The loop formed can be engaged with the root of the affected part 27, as shown in FIG. 10.

Figure 11:
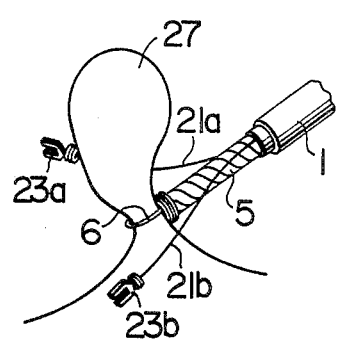
Figure 12:
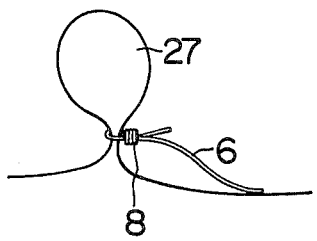

Then the tying operator 13 can be moved rearwardly or to a position shown in phantom lines in FIG. 3, whereby the pulling end 9 is pulled by the operating wire 11 to reduce the size of the loop, thereby strongly binding the root of the affected part 27, as illustrated in FIG. 11. This prevents a circulation of the blood to the affected part 27. Subsequently, the pulling end 9 may be cut by a scissor forceps to leave the ligature 6 within the coeloma, as shown in FIG. 12.

In the process of reducing the size of the loop formed by the loop formation 7, the constraint applied by the opening 24 of the holding wires 21a, 21b to the thread portions of the loop formation 7 will be reduced less than the tension in the latter to thereby allow its desengagement from the captures 23 when the loop size is reduced below that indicated by phantom lines 7A in FIG. 9. As a consequence, when the root of the affected part 27 is bound by the ligature 6 as indicated by phantom lines 7B in FIG. 9 in FIG. 11, the holding wires will be completely disengaged from the ligature 6, so that only the ligature 6 remains within the coeloma.

Figure 13:
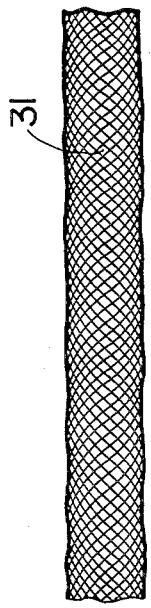
FIG. 13 is a fragmentary enlarged plan view of one example of the ligature which comprises knitted filaments.
Figure 14:
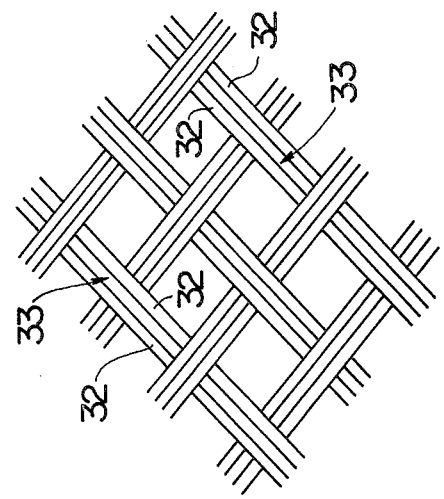
FIG. 14 is a fragmentary plan view, enlarged to a microscopic scale, of the example shown in FIG. 13.

FIG. 13 shows a portion of a preferred ligature 31 which can be advantageously used in the apparatus of the invention for improving the formation of a loop. The ligature 31 comprises a knitting of a filamentary material 33 which comprises either single or multiple filaments 32 as shown in FIG. 14, which, for example, illustrates a plain stitch. However, it should be understood that the preferred ligature is not limited to any particular stitch. In this manner, a twisting of the ligature upon being wetted by moisture or body fluid is prevented, facilitating the formation of the loop in a desirable form. While such knitted ligature can be useful in a ligation apparatus having no holding wires, it is most effective when used in the apparatus of the invention.

Figure 15:
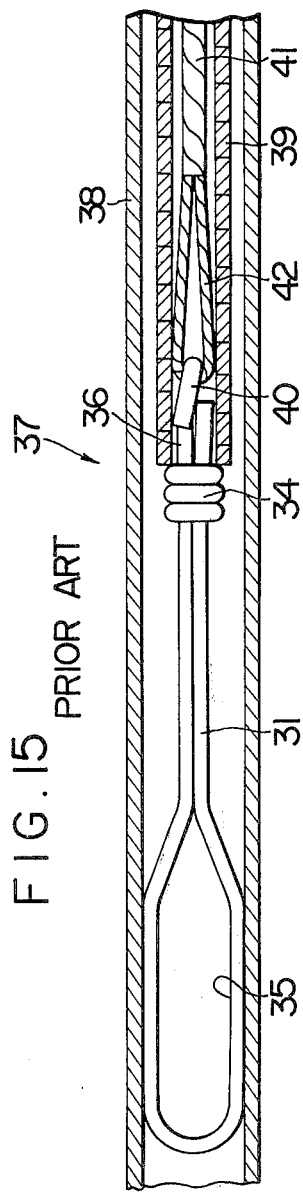
FIG. 15 is a fragmentary longitudinal section of a ligation apparatus having no holding wires.

An application of the preferred ligature 31 in a ligation apparatus having no holding wires will be described with reference to FIG. 15, wherein a ligation apparatus 37 comprises an outer flexible tube 38 and an inner flexible tube 39 formed as a close pitched coil and which extends therethrough. A loop formation 35 of the ligature 31 is received within the outer tube 38 adjacent to the distal end of the inner tube 39. A knot 34 is formed in the ligature, and the opening in the distal end of the inner tube 39 has a size such that the knot 34 cannot be moved into the interior of the inner tube 39. The ligature 31 has a pulling end 36 which is folded within the inner tube 39 as shown at 40 for engagement with a hook 42 formed at the inner end of an operating wire 41 which extends through the inner tube 39.

The other end of the operating wire 41 extends to a manual operation section, not shown, for allowing the ligature to be pulled externally of the coeloma. The outer tube 38 is also adapted to be operated at the manual operation section so as to be moved relative to the inner tube 39. When the outer tube 38 is retracted relative to the inner tube, the loop formation 35 in the ligature 31 is exposed externally of the outer tube 38, whereby it is free to be extended into a loop of a greater size. Subsequently, the operating wire 41 may be pulled to move the pulling end 36 of the ligature 31 further into the inner tube 39 through the hook 42, thus reducing the size of the loop formed by the loop formation 35.

What is claimed is:

1. An apparatus for ligation of an affected part in coeloma comprising a ligature having a loop formation which is adapted to form a loop for ligating an affected part in an coeloma, the loop being reduced in size by pulling one end of the loop formation; an inner flexible tube into which said one end of the ligature extends; a pair of holding wires each having one end mounted on a distal end portion of the inner tube and having a free end formed as a capture for releaseably engaging the loop formation, the captures being effective to retain the loop formation therein below a given level of tension in the loop formation; and an outer flexible tube for internally housing the loop formation, the holding wires and the inner flexible tube in compacted condition; said outer flexible tube adapted for insertion into a coeloma, the outer tube being adapted to be operated for displacement in a direction to expose the loop formation and the holding wires into the coeloma, the holding wires being resiliently biased in a manner such that their respective captures are effective to extend the loop formation into a loop of an increased size when it is exposed while maintaining engagement with the captures.

2. An apparatus according to claim 1 in which the ligature is formed of a knitted material.

3. An apparatus according to claim 1 in which the holding wires comprise resilient metal wires.

4. An apparatus according to claim 3 in which the capture of the holding wires is integrally formed in the holding wires by bending the material of the holding wires.

5. Apparatus for ligation of an affected part comprising:

a first assembly including a ligature, a first flexible tubular member, movable means positioned within said tubular member, and a pair of resilient wire-like elements;

said ligature having a first and a second end, said first end being slidably knotted about said ligature to form a knot therein;

said first flexible tubular member having an open end;

said ligature second end extending at least partially into said open end of said first tubular member;

said movable means positioned in said first tubular member and axially slidable therethrough, one end of said movable means being joined to said second end of said ligature;

said open end of said first tubular member being of a size adapted to prevent said knotted first end of said ligature from entering into said first tubular member;

said pair of resilient wire-like elements having their first ends secured to said first tubular member and having releasable gripping means at their opposite free ends for releasable gripping portions of said ligature at spaced locations along said loop;

a second hollow tubular member for slottedly receiving said first assembly; and;

means for axially moving said first assembly relative to said second hollow tubular member to project said loop and said free ends of said wire-like elements beyond one end of said second hollow tubular member, the free ends of said resilient wire-like elements being biased radially outward with respect to said second hollow tubular member whereby said free ends of said wire-like elements move away from one another to increase the distance between said gripped portions of said ligature as said wire-like elements are further extended from said one end of said second hollow tubular member to facilitate encirclement of an affected part by said loop.

6. The apparatus of claim 5 wherein the size of said loop is reduced by pulling said ligature second end more deeply into said first tubular member by operation of said movable means thereby moving the gripped portions of said loop closer together; said gripping means being adapted to release the gripped portions of the loop when the size of the loop is reduced by a predetermined amount.

7. The apparatus of claim 6 wherein said elements comprise resilient metallic wires.

8. The apparatus of claim 7 wherein said free ends are bent to form a substantially C-shaped gripping structure for releasably gripping said ligature.

9. The apparatus of claim 5 wherein said ligature is formed of a knitted material.

* * * * *